United States Patent [19]

Toy et al.

[11] 4,034,024

[45] July 5, 1977

[54] METHOD OF PREPARING TRIALKYL TETRATHIOPHOSPHATES

[75] Inventors: Arthur D. F. Toy, Stamford, Conn.; Eugene H. Uhing, Ridgewood, N.J.

[73] Assignee: Stauffer Chemical Company, Westport, Conn.

[22] Filed: Jan. 19, 1976

[21] Appl. No.: 650,488

Related U.S. Application Data

[63] Continuation of Ser. No. 514,525, Oct. 15, 1974, abandoned.

[52] U.S. Cl. .............................................. 260/981
[51] Int. Cl.$^2$ ..................... C07F 9/17; C07F 9/177
[58] Field of Search ................................... 260/981

[56] References Cited

UNITED STATES PATENTS

| 3,328,360 | 6/1967 | Rozanski et al. | 260/981 X |
| 3,487,131 | 12/1969 | Worrel | 260/981 |

OTHER PUBLICATIONS

Houben–Weyl, Methoden der Organischen Chemie, vol. 12/2 (1964), p. 747.

*Primary Examiner*—Richard L. Raymond
*Attorney, Agent, or Firm*—William R. Robinson

[57] ABSTRACT

Trialkyl tetrathiophosphates are prepared by contacting a dialkyl sulfide with phosphorus pentasulfide according to the following theoretical reaction scheme:

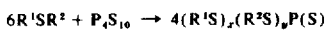

$$6R^1SR^2 + P_4S_{10} \rightarrow 4(R^1S)_x(R^2S)_yP(S)$$

wherein $x + y = 3$; $R^1$ and $R^2$ are the same or different and are selected from the group consisting of aliphatic, having from 1 to about 18 carbon atoms, and alicyclic having 5 or 6 carbon atoms in the ring and the $C_1$–$C_4$ alkyl substituted derivatives thereof. The contacting is effected under at least autogenous pressure at a temperature of from about 150° C. to 300° C. The compounds obtained are useful as additives in agricultural chemicals and as intermediates in preparation of other organophosphorus compounds.

5 Claims, No Drawings

METHOD OF PREPARING TRIALKYL TETRATHIOPHOSPHATES

This is a continuation of application Ser. No. 514,525 filed Oct. 15, 1974, now abandoned.

BACKGROUND OF THE INVENTION

1. Field of the Invention

The present invention relates to a new and improved method of preparation of trialkyl tetrathiophosphates.

2. The Prior Art

Tetrathiophosphates have been prepared in the prior art by reacting lead thiolates with thiophosphoryl chloride according to the following general reaction scheme:

$$Pb(SR)_2 + P(S)Cl_3 \rightarrow (RS)_3P(S) + R_2S_2 + PbCl_2 \quad (2)$$

wherein R is selected from the group consisting of $CH_3$, $C_2H_5$, n-$C_4H_9$, o-$CH_3C_6H_4$, p-$CH_3C_5H_4$ and p-$ClC_6H_4$. Under reaction (2), trialkyl tetrathiophosphates are prepared in boiling benzene whereas triaryl tetrathiophosphates can only be obtained in boiling xylene.

Another reaction is observed for thiolates, namely:

$$Pb(SR)_2 + P(S)Cl_3 \rightarrow PbS + R_2S_2 + PCl_3 \quad (3)$$

wherein R is selected from the group consisting of $CH_2C_6H_5$, $C_6H_5$, m—$CH_3C_6H_4$. These reactions are described in *Phosphorus*, R. A. Shaw and M. Woods, Vol. 1, Part 1, (Oxford, England, 1971) p. 42.

Other known methods of preparing tetrathiophosphates include the reaction of thiophosphoryl chloride with either a thiol or a sodium thiolate and the reaction of phosphorus pentasulfide and thiols.

SUMMARY OF THE INVENTION

In accordance with the present invention, there is provided a new method of preparing compounds of the formula:

$$(R^1S)_x(R^2S)_yP(S) \quad I$$

wherein $x + y = 3$; $R^1$ and $R^2$ are the same or different and are selected from the group consisting of aliphatic groups having from 1 to about 18 carbon atoms and alicyclic of 5 to 6 carbons in the ring and the $C_1$-$C_4$ alkyl substituted derivatives thereof. The aliphatic groups include $C_1$-$C_{18}$ straight-chain or branched alkyl groups and the alicyclic groups include cycloalkyl of 5 to 6 carbons in the ring and the $C_1$-$C_4$ alkyl substituted derivatives thereof.

Exemplary R groups include methyl, ethyl, n-propyl, isopropyl, n-butyl, isobutyl, tert-butyl, pentyl, hexyl, heptyl, octyl, nonyl, decyl, dodecyl, tetradecyl, hexadecyl, octadecyl, cyclohexyl and cyclopentyl and the $C_1$-$C_4$ alkyl substituted derivatives thereof.

The method comprises contacting a dialkyl sulfide reactant of the formula:

$$R^1SR^2 \quad II$$

wherein $R^1$ and $R^2$ are as defined above, with phosphorus pentasulfide having the formula:

$$P_4S_{10} \quad III$$

The following equation (1) is representative of the reaction:

$$6R^1SR^2 + P_4S_{10} \rightarrow 4(R^1S)_x(R^2S)_yP(S) \quad (1)$$

where $x + y = 3$. In the event that $R^1$ and $R^2$ are different, a mixed product results and thus $x$ can be 0, 1, 2 or 3 and $y$ can be 0, 1, 2 or 3 as long as the sum of $x$ and $y$ is equal to 3.

Reactants utilized in the process of the present invention can be employed in stoichiometric amounts, although an excess of either reactant can be used if desired.

The process of the present invention is carried out at elevated temperature and at least at autogenous pressure and preferably at a pressure of between about 1 and 300 atmospheres. Temperatures of between about 150° to about 300° C. can be used though temperatures of about 180° C. to about 250° C. are preferred.

The trialkyl tetrathiophosphate products of the present invention are known and have utility as additives, agricultural chemicals, pharmaceutical chemicals and as intermediates in the preparation of other organophosphorus compounds. For example, trialkyl tetrathiophosphates are used as anti-wear additives in lubricating oils and as additives to fuel for improving surface ignition control in engines operating in the Otto cycle. Also, the products are known to have synergistic effects when used with certain pharmaceuticals and insecticides.

The method of the present invention may conveniently be effected by introducing the individual reactants into a reaction zone; equipped with an agitation means (a rocker, vibrator or stirrer) for best results. When low boiling dialkyl sulfides are used, for example dimethyl sulfide, the reaction zone must be capable of withstanding elevated pressure. Pressure vessels such as metal bombs, autoclaves and the like or a vessel kept under an inert atmosphere, such as nitrogen, at a pressure sufficient to prevent the dialkyl sulfide from being lost by distillation are suitable for this purpose. The reaction is carried out under at least the autogenous pressure developed by the reactants at the reaction temperature. Pressures of up to 100 atmospheres above the autogenous pressure can also be used, but are less desirable due to the inconvenience of requiring a pressurization system. When higher boiling dialkyl sulfides are used, for example dioctyl sulfide, no pressure vessel is required. The reaction may be carried out in a continuous or batchwise system as desired.

Reaction times vary over relatively wide ranges depending upon reaction temperature and the reactivity of the dialkyl sulfide. Generally, higher reaction temperatures require a shorter reaction time and low boiling dialkyl sulfides require longer reaction times than high boiling dialkyl sulfides. For example, dimethyl sulfide requires a longer reaction time than the longer chain dialkyl sulfides. Times of reaction can easily be determined by one skilled in the art. Typical reaction times are between 1 and about 24 hours. Preferred reaction times are between about 2 and about 12 hours.

The products of the reaction are purified by conventional methods such as distillation, filtration, sublimation and extraction.

The identification of products is achieved by conventional methods such as elemental analysis, gas chromatography, refractive index and nuclear magnetic resonance ($^{31}$P-nmr and H-nmr).

Illustrative of the compounds which can be prepared by the method of the present invention are:

(CH$_3$S)$_2$(C$_2$H$_5$S)P(S)
(CH$_3$S)(C$_2$H$_5$S)$_2$P(S)
(C$_3$H$_7$S)$_2$(CH$_3$S)P(S)
(C$_3$H$_7$S)(C$_2$H$_5$S)$_2$P(S)
(CH$_3$S)$_2$(C$_4$H$_9$S)P(S)
(CH$_3$S)(C$_4$H$_9$S)$_2$P(S)
(C$_4$H$_9$S)$_2$(C$_3$H$_7$S)P(S)
(C$_5$H$_{11}$S)$_2$(CH$_3$S)P(S)
(CH$_3$S)$_3$P(S)
(C$_2$H$_5$S)$_3$P(S)
(C$_3$H$_7$S)$_3$P(S)
(C$_4$H$_9$S)$_3$P(S)
(C$_5$H$_{11}$S)$_3$P(S)
(C$_6$H$_{17}$S)$_3$P(S)
(C$_{18}$H$_{37}$S)$_3$P(S)

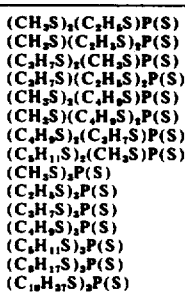

The following examples are submitted to illustrate but not to limit the present invention.

EXAMPLE I $$6(CH_3)_2S + P_4S_{10} \rightarrow 4(CH_3S)_3P(S)$$

In a 300 ml 316 stainless steel autoclave were placed 30 grams (CH$_3$)$_2$S (0.48 mole) and 35.5 grams P$_4$S$_{10}$ (0.08 mole). The autoclave was heated at 250° C. for 12 hours. After cooling, the pour out yield of liquid was 62.5 grams. The crude product was analyzed by mass spectra which showed the following components to be present:
1. Major: (CH$_3$S)$_3$P(S)
2. Sub-major: (CH$_3$S)$_2$P(S)CH$_3$
3. Minor:
  a. CS$_2$,
  b. CH$_3$SSCH$_3$,
  c. CH$_3$S$_3$CH$_3$,
  d. CH$_3$SP(S) (CH$_3$)$_2$
  e. plus other minor components.

The crude product was distilled to give 13.5 grams product (b.p. 100°–105° C. at 0.3 mm) having the following assay by H-nmr:
(CH$_3$S)$_3$P(S); 82.9 mole %.
(CH$_3$S)$_2$P(S)CH$_3$; b 17.1 mole %.

EXAMPLE II

Tl $6(C_2H_5)_2S + P_4S_{10} \rightarrow 4(C_2H_5S)_3P(S)$

In a 300 ml stainless steel autoclave were placed 27 grams (C$_2$H$_5$)$_2$S (0.3 mole) and 22.2 grams P$_4$S$_{10}$ (0.05 mole). The autoclave was heated at 240° C. for 12 hours. The yield of crude product was 46 grams. Analysis by hu 31 P-nmr spectroscopy showed that the yield of (C$_2$H$_5$S)$_3$P(S) was 53.2% (Chemical Shift from H$_3$PO$_4$ = −91.4 ppm. The crude product was distilled (b.p = 110°–175° at 0.1 mm Hg; $n_D^{20}$ = 1.6169) to give 22 grams product (45% yield) which assayed 97% (C$_2$H$_5$S)$_3$P(S) by $^{31}$P-nmr analysis.

EXAMPLE III $$6(C_2H_5)_2S + P_4S_{10} \rightarrow 4(C_2H_5S)_3PS$$

Example II was repeated at a lower reaction temperature and in a glass Carius tube as follows:
In a 3 ml glass Carius tube were placed 1.19 grams (C$_2$H$_5$)$_2$S (0.013 mole) and 0.97 grams P$_4$S$_{10}$ (0.0022 mole). The tube was sealed and placed in an autoclave along with methyl alcohol to equalize the pressure in the Carius tube during heating. The autoclave was heated at 210°–220° for 12 hours. The product was analyzed by $^{31}$ P-nmr spectroscopy which showed only one major phosphorus component; (Chemical Shift from H$_3$PO$_4$ = −92.1 ppm) (C$_2$H$_5$S)$_3$P(S) to be present in 88 mole % yield.

EXAMPLE IV $$6(C_2H_5)_2S + P_4S_{10} \rightarrow 4(C_2H_5S)_3PS$$

Example III was repeated at shorter reaction times as follows:
On each of two 3 ml glass Carius tubes were placed 1.09 grams (C$_2$H$_5$)$_2$S (0.012 mole) and 0.9 grams P$_4$S$_{10}$ (0.002 mole. Each tube was sealed and placed in an autoclave along with methyl alcohol to equalize pressure and heated to 210° C. One tube was heated for 8 hours and the other tube for 1 hour. The products were analyzed by $^{31}$ P-nmr spectroscopy and gave the following results:

| Tube | Heating Time at 210° C. Hours | Mole % (C$_2$H$_5$S)$_3$P(S) (Chemical Shift from H$_3$PO$_4$ = −92.2 ± .1 ppm) |
|---|---|---|
| 1 | 8 | 82 |
| 2 | 1 | 63 |

EXAMPLE V $$6(n-C_4H_9)_2S + P_4S_{10} \rightarrow 4(C_4H_9S)_3P(S)$$

In a 300 ml stainless steel autoclave were placed 43 grams (n-C$_4$H$_9$)$_2$S (0.29 mole and 22 grams P$_4$S$_{10}$ (0.049 mole). The autoclave was heated at 240° C. for 12 hours. The yield of crude product was 62 grams. The crude product was distilled to give 33.5 grams of product (bp=145°–180° C. at 0.1 mm Hg); $n_D^{20}$ = 1.5822) which by $^{31}$P-nmr analysis consisted of two major (C$_4$H$_9$S)$_3$P(S) components. These components are due to isomers of the —C$_4$H$_9$ group present in (C$_4$H$_9$S)$_3$P(S).

EXAMPLE VI $$6(n-C_4H_9)_2S = P_4S_{10} \rightarrow 4(C_4H_9S)_3P(S)$$

Example V was repeated at a lower temperature and in a glass Carius tube as follows:
In a 3 ml glass Carius tube were placed 1.343 grams (n-C$_4$H$_9$)$_2$S (0.009 mole) and 0.68 gram P$_4$S$_{10}$ (0.0015 mole). The tube was sealed and placed in an autoclave along with methyl alcohol to equalize pressure and heated at 210°–220° C. for 12 hours. The crude product was analyzed by $^{31}$P-nmr spectroscopy and gave the following results:

| Chemical Shift from $H_3PO_4$ ppm | Chemical Assignment | Mole % |
|---|---|---|
| −103.5 | Unknown | 9.2 |
| −102.7 | Unknown | 12.6 |
| −93.5 | $(C_8H_9S)_3P(S)$ | 53.0 |
| −91.9 | Isomers of $(C_8H_9S)_3P(S)$ | 16.1 |
| −90.4 | Unknown | 5.7 |
| −78.9 | Unknown | 3.4 |

EXAMPLE VII $$6(n\text{-}C_8H_{17})_2S + P_4S_{10} \rightarrow 4(C_8H_{17}S)_3P(S)$$

In a 3 ml glass Carius tube were placed 1.349 grams $(n\text{-}C_8H_{17})_2S$ (0.00523 mole) and 0.414 grams $P_4S_{10}$ (0.009 mole). The sealed tube was placed in an autoclave and heated at 210°-220° C. for 12 hours. The product was analyzed by $^{31}$P-nmr spectroscopy and gave the following results:

| Chemical Shift from $H_3PO_4$ ppm | Compound Assignment | Mole % |
|---|---|---|
| −93.6 | $(C_8H_{17}S)_3P(S)$ | 75 |
| −91.9 | Isomers of $(C_8H_{17}S)_3P(S)$ | 12.5 |
| −90.4 | Isomers of $(C_8H_{17}S)_3P(S)$ | 12.5 |

EXAMPLE VIII $$6(n\text{-}C_8H_{17})_2S + P_4S_{10} \rightarrow 4(C_8H_{17}S)_3P(S)$$

Example VII was repeated at atmospheric pressure as follows:

In a 25 ml 3-neck pyrex reaction flask provided with a reflux condenser, thermometer and sampling dip tube were placed, while stirring with a magnetic bar, 13.9 grams $(n\text{-}C_8H_{17})_2S$ (0.0539 mole) and 3.99 grams $P_4S_{10}$ (0.00898 mole). The reaction was kept under an atmosphere of nitrogen while heating at 220° C. Samples were removed during the reaction and analyzed by $^{31}$P-nmr spectroscopy.

| Hours Heated at 220° C. | Mole % $(C_8H_{17}S)_3P(S)$ (Chemical Shift from $H_3PO_4 = -92.4 + 0.2$ ppm) |
|---|---|
| 1 | 19 |
| 1.5 | 27.5 |
| 2.0 | 31.0 |
| 5.0 | 40.0 |

There were 10 other phosphorus products present after heating at 220° C. for 5 hours as shown by the $^{31}$P-nmr spectra.

EXAMPLE IX $$6C_4H_9SCH_3 + P_4S_{10} \rightarrow (CH_3S)_3P(S) + (CH_3S)_2(C_4H_9S)P(S) + (C_4H_9S)_3P(S)$$

In a 3 ml glass Carius tube were placed 1.25 grams $C_4H_9SCH_3$ (0.012 moles) and 0.89 grams $P_4S_{10}$ (0.002 moles). After sealing, the tube was placed in an autoclave along with methyl alcohol to equalize pressure and heated to 210° C. for 6 hours. The product was analyzed by $^{31}$P-nmr spectroscopy which gave the following results.

| Chemical Shift from $H_3PO_4$ ppm | Compound Assignment | Mole % |
|---|---|---|
| −98.9 | Unknown | 9.8 |
| −98.3 | Unknown | 3.3 |
| −97.3 | $(CH_3S)_3P(S)$ | 27.7 |
| −96.2 | Unknown | 6.0 |
| −95.2 | Mixed $(CH_3S)_2(C_4H_9S)P(S)$ and $(CH_3S)(C_4H_9S)_2P(S)$ | 32.6 |
| −94.5 | Unknown | 6.0 |
| −93.5 | $(C_4H_9S)_3P(S)$ | 14.7 |

The present invention is defined in the following claims.

What is claimed is:

1. A method of preparing compounds of the formula:

$$(R^1S)_x(R^2S)_yP(S) \qquad (1)$$

wherein $x + y = 3$; $R^1$ and $R^2$ are the same or different and are selected from the group consisting of $C_1$-$C_{18}$ straight-chain or branched alkyl and cycloalkyl of 5 to 6 carbons in the ring and the $C_1$-$C_4$ alkyl substituted derivatives thereof; comprising contacting under at least an autogenous pressure at a temperature of from about 150° C. to 300° C. a reactant selected from the group consisting of dialkyl sulfide reactants of the formula:

$$R^1SR^2 \qquad \text{II}$$

wherein $R^1$ and $R^2$ are as defined above with a phosphorus pentasulfide reactant of the formula:

$$P_4S_{10}.$$

2. The method of claim 1 wherein $R^1$ and $R^2$ are the same or different and are selected from the group consisting of methyl, ethyl, n-propyl, isopropyl, n-butyl, isobutyl, tertbutyl, pentyl, hexyl, heptyl, octyl, nonyl, decyl, dodecyl, tetradecyl, hexadecyl, octadecyl, cyclopentyl, cyclohexyl and ethylcyclohexyl.

3. The method of claim 1 wherein $R^1$ and $R^2$ are the same and are selected from the group consisting of methyl, ethyl, n-propyl, isopropyl, n-butyl, isobutyl, tert-butyl, pentyl, hexyl, heptyl, octyl, nonyl, decyl, dodecyl, tetradecyl, hexadecyl, octadecyl, cyclopentyl, cyclohexyl and ethylcyclohexyl.

4. The method of claim 1 wherein said autogenous pressure is between about 1 and about 300 atmospheres.

5. The method of claim 1 wherein said reactants are employed in stoichiometric amounts according to the following equation:

$$6R^1SR^2 + P_4S_{10} \rightarrow 4(R^1S)_x(R^2S)_yP(S)$$

wherein $x, y, R^1$ and $R^2$ are as defined in claim 1.

* * * * *